United States Patent
Boerner et al.

(10) Patent No.: US 6,838,070 B1
(45) Date of Patent: Jan. 4, 2005

(54) METHOD OF PRODUCING CYANURIC CHLORIDE

(75) Inventors: Walter Boerner, Freigericht (DE); Ralph Marquardt, Frankfurt am Main (DE); Stephanie Schauhoff, Frankfurt am Main (DE); Christine Schick, Offenbach (DE); Rudolf Vanheertum, Brasschaat (BE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/926,295
(22) PCT Filed: Mar. 8, 2000
(86) PCT No.: PCT/EP00/02013
§ 371 (c)(1), (2), (4) Date: Oct. 9, 2001
(87) PCT Pub. No.: WO00/64879
PCT Pub. Date: Nov. 2, 2000

(30) Foreign Application Priority Data

Apr. 22, 1999 (DE) .......................... 199 18 245

(51) Int. Cl.$^7$ ............................... C01C 3/00
(52) U.S. Cl. .................... 423/371; 423/383; 423/445 R; 502/180
(58) Field of Search .......................... 502/180; 423/371, 423/445 R, 383

(56) References Cited

U.S. PATENT DOCUMENTS

| | | | | |
|---|---|---|---|---|
| 3,018,288 A | * | 1/1962 | Tokime et al. | 502/180 |
| 3,312,697 A | | 4/1967 | Reithmann | |
| 3,533,961 A | * | 10/1970 | Voet et al. | 502/180 |
| 3,707,544 A | | 12/1972 | Suryanarayana et al. | |
| 3,789,021 A | * | 1/1974 | Suryanarayama e al. | 502/180 |
| 3,867,382 A | | 2/1975 | Suryanarayana et al. | |
| 3,944,656 A | * | 3/1976 | Durrell et al. | 423/371 |
| 4,029,600 A | * | 6/1977 | Schmitt, Jr. et al. | 502/180 |
| 4,978,649 A | * | 12/1990 | Surovikin et al. | 502/180 |
| 6,064,560 A | * | 5/2000 | Hirahara et al. | 502/180 |
| 6,114,280 A | * | 9/2000 | Stephens | 502/180 |

* cited by examiner

Primary Examiner—Wayne A. Langel
(74) Attorney, Agent, or Firm—Oblon, Spivak, McClelland, Maier & Neustadt, P.C.

(57) ABSTRACT

The invention relates to a method of producing cyanuric chloride by trimerizing chlorocyan at a temperature of at least 250° C. on washed activated carbon as the catalyst. The service life of the catalyst can be improved by using an activated coal with an effective pore volume V eff of equal or greater 0.17 ml/g, with V eff being the result of pores with a pore diameter ranging from 0.5 to 7 nm.

5 Claims, 1 Drawing Sheet

Movement of the hot spot through the reactor

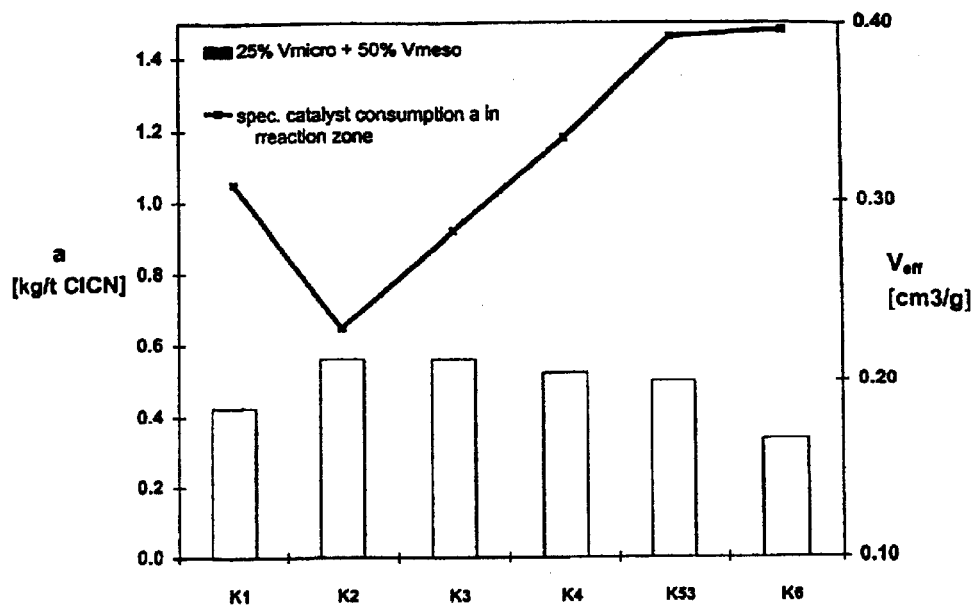
Fig. 1: Specific catalyst consumption a in relation to the effective pore volume
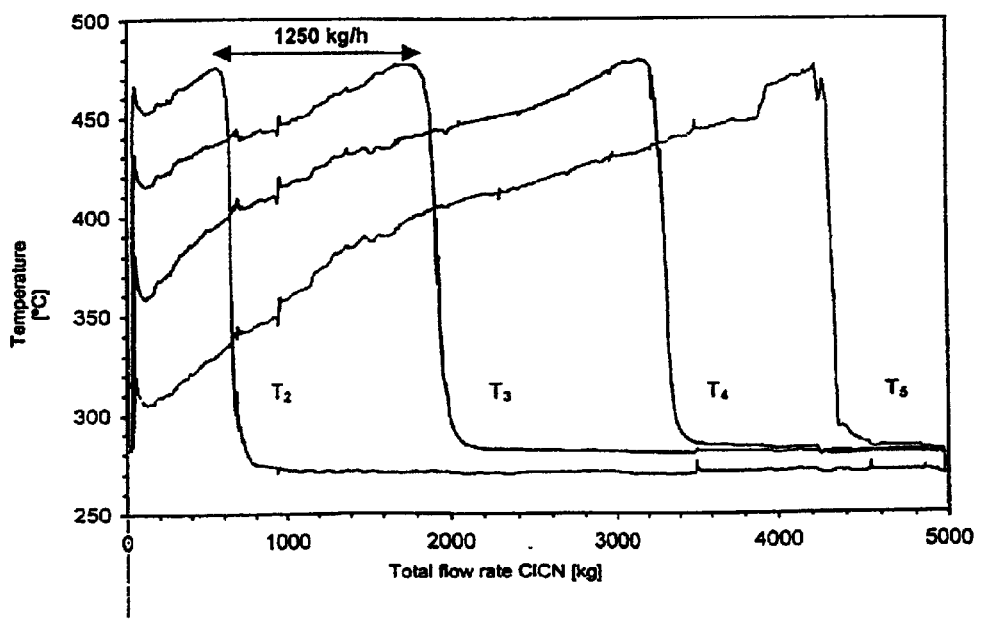
Fig. 2: Movement of the hot spot through the reactor

METHOD OF PRODUCING CYANURIC CHLORIDE

This invention relates to a process for producing cyanuric chloride by trimerisation of cyanogen chloride at a temperature of above 200° C. on an activated carbon catalyst. The process according to the invention also results in a decreased specific catalyst consumption.

DISCUSSION OF THE BACKGROUND

Cyanuric chloride is produced on a large scale by chlorination of hydrogen cyanide with the formation of cyanogen chloride and trimerisation of the cyanogen chloride to form cyanuric chloride—see Ullmann's Encyclopedia of Industrial Chemistry Vol. A8, $5^{th}$ ed. (1987), 196–197. The trimerisation is carried out in the vapour phase at a temperature of above 200° C., in particular in the range of about 300 to 450° C., on an activated carbon catalyst. During continuous operation, a temperature profile develops along the longitudinal axis of the reactor owing to the exothermicity of the trimerisation reaction; this results in the formation of a so-called hot-spot, the temperature maximum of which depends on the flow rate and rises with increasing flow rate. It is known that the deactivation of the activated carbon catalyst is influenced by the operating conditions, the flow rate and the quality of the activated carbon. The deactivation becomes apparent from the movement of the reaction zone, and with it the temperature maximum, along the longitudinal axis of the catalyst.

Owing to its becoming deactivated, the catalyst has to be exchanged periodically or otherwise activated. The economic efficiency of the cyanuric chloride process depends considerably on the service life of the catalyst, as not only the cost of the catalyst but also the cost of a plant standstill have to be taken into account. Moreover, with increasing deactivation of the catalyst, secondary products such as, for example, cyameluric chloride, are increasingly discharged and hence necessitate increased expenditure on the purification of the cyanuric chloride.

In view of the problems demonstrated, the experts have for a long time been interested in finding activated carbon catalysts which have an increased service life and/or in varying the operating conditions in such a way that the service life can be increased.

Accordingly, U.S. Pat. No. 3,312,697 discloses a process for producing cyanuric chloride using an activated carbon catalyst having a specific surface of above 1000 $m^2/g$, in which the activated carbon catalyst was activated by a treatment with acids and/or alkalies and a downstream washing with water. As a result of the above-mentioned treatment, inorganic constituents such as oxides, hydroxides and salts of metals such as Li, Mg, Ce, Ti, V, Mn, Fe, Ni, Pt, Cu, Zn, Cd, Sn, Pb and Bi, which diminish the service life of the catalyst, are dissolved out of the activated carbon. The service life of the catalyst is further increased in this process by the addition of 0.5 to 10 wt. % chlorine and/or phosgene to the cyanogen chloride.

In the process according to U.S. Pat. No. 3,707,544, the service life is increased by mixing the trimerisation reactor with a mixture of an activated carbon and a solid diluent having little or no catalytic activity. The disadvantage of this process is that the space-time yield is diminished and the expense of disposing of the deactivated catalyst is increased, above all if the diluent is a non-combustible material.

In the process described in U.S. Pat. No. 3,867,382, an untreated activated carbon produced from coconut shells is used instead of an acid-washed activated carbon. This activated carbon has an internal surface area of 1200 to 1500 $m^2/g$, a micropore volume of at least 0.7 $cm^3/g$ and an ash content of below 4 wt. %. Owing to the vegetable origin of the raw material used for this activated carbon, it has a low content of heavy metals and an acid wash is rendered unnecessary. It cannot be inferred from this document how the micropores are defined, i. e. whether they comprise all the internal pores, or micropores having precisely defined limiting values for the pore diameters. A considerable disadvantage of the activated carbon used in the examples is that the bulk density, and hence the quantity required based on the reactor volume, is very high and thus diminishes the economic efficiency.

In J. Beijing Inst. Chem. Technol. 20 (1993) 1, 55–58, E. Wang et al. explain that several factors, namely, the ash content, the iron content, the specific surface and the pore-size distribution, have to be taken into account when selecting the catalysts for the cyanogen chloride trimerisation. The selection of a suitable activated carbon is complicated by the fact that these factors may mutually influence one another. It is to be concluded from this document that it is advantageous to use a carbon which has as high a specific surface as possible and therefore contains numerous small pores. The latter help to enable the reaction to proceed on a relatively large number of active centres. From the diagrams of the pore-size distribution of two different activated carbons, it is suggested that the pores should have a diameter in particular of less than 2 nm. However, no information can be drawn from the document as to how the individual factors influence the service life of the catalyst in a production plant designed for continuous operation.

BRIEF SUMMARY OF THE INVENTION

Accordingly, the object of the present invention is to demonstrate an improved process for producing cyanuric chloride by trimerisation of cyanogen chloride, the improvement consisting in a decreased specific catalyst consumption. A further object is to demonstrate the criteria whereby the person skilled in the art can select an activated carbon catalyst having an extended service life for this type of reaction. Other objects can be inferred from the following description of the process according to the invention.

BRIEF DESCRIPTION OF THE DRAWINGS

FIG. 1: Specific catalyst consumption a in relation to the effective pore volume FIG. 2: Movement of the hot spot through the reactor

DETAILED DESCRIPTION OF THE INVENTION

A process for producing cyanuric chloride has been found, comprising trimerisation of cyanogen chloride in the presence of a washed activated carbon having a BET surface area of at least 1000 $m^2/g$ and an Fe content (calculated as $Fe_2O_3$) of less than 0.15 wt. % at a temperature of at least 250° C., which is characterised in that an activated carbon having an effective pore volume $V_{eff}$ of equal to or greater than 0.17 ml/g is used, $V_{eff}$ being obtained from pores having a pore diameter in the range of 0.5 to 7 nm. The subclaims are directed towards preferred embodiments of the process.

It was found that the trimerisation of cyanogen chloride proceeds satisfactorily only in those pores having pore diameters in the range of 0.5 to 7 nm, in particular 0.5 to 5 nm; the pore volume of these pores are to be at least 0.17 ml/g. Although the pore distribution of activated carbons can differ very widely depending upon the conditions of their production, the effective pore volumes $V_{eff}$ necessary for the reaction can be defined from the sum of a volume increment for the micropores having a pore diameter of <2 nm and a volume increment of the mesopores having a pore diameter of 2 to 30 nm. The effective pore volume accordingly can be represented as a linear function: $V_{eef}=a \cdot V_{micro}+b \cdot V_{meso}$. It was also found that the function $V_{eff}=0.25 \cdot 0.50\ V_{micro}+V_{meso}$ is a suitable selection criterion for an effective activated carbon having a long service life. The volumes of the micro- and mesopores are determined as follows:

The micropore volume is determined from the nitrogen adsorption isotherm at the temperature of liquid nitrogen by comparison with a standard isotherm using the t-plot process of De Boer (cf. De Boer et al. in J. of Colloid and Interface Science 21, 405-44 (1966)) in accordance with DIN 66135, Part 2 (Version of April 1998).

The mesopore volume and the pore distribution are determined from the nitrogen desorption isotherm of Barett, Joyner and Halenda in accordance with DIN 66134 (February 1998). Prior to the measurement, the sample used for the determination of $V_{micro}$ and $V_{meso}$ is treated for 1 h at 200° C. under vacuum (less than 1.3 Pa). The measurement is carried out, for example, in an "ASAP 2400" instrument manufactured by the firm of Micromeritics, Norcross, Ga. (US). The definition of $V_{meso}$ according to the invention includes only mesopores having a diameter of 2 to 30 nm.

A particularly large increase in the service life of the activated carbon in this type of process is achieved if $V_{eff}$ is at least 0.2 ml/g. From an investigation of numerous different activated carbons, it was found that a maximum value of the effective pore volume defined above corresponds to a minimum value of the specific catalyst consumption. Both extremely mesoporous activated carbons and extremely microporous activated carbons have too low a pore volume in the middle pore range, that is, in the range between 0.5 and 5 nm, so that the specific catalyst consumption is considerably higher than in the catalysts to be used according to the invention.

Another feature of the activated carbons to be used according to the invention is the specific surface(BET surface area), which is at least 1000 m²/g, preferably at least 1200 m²/g. A high surface area is consequently advantageous, but is not a criterion which allows a conclusion regarding the service life of the catalyst. Thus, different activated carbons having virtually identical specific surfaces exhibit very large differences in their rates of deactivation.

In view of the negative influence of a high iron content on the activated carbon, the iron content, calculated as $Fe_2O_3$, should be below 0.15 wt. % and preferably around or below 0.1 wt. %. Although an unwashed activated carbon is also catalytically active, in the process according to the invention a washed, in particular an acid-washed, activated carbon is used, because washing is on the one hand a possible way of decreasing the content of iron and of the other heavy metals and hence of minimising the formation of secondary products and, on the other hand, it increases the pore volume, which is important for the reaction. With regard to the minimisation of the specific catalyst consumption, it is moreover advantageous to use a carbon having a bulk density of equal to or less than 420 g/l. Where the activity of the activated carbon catalyst is adequate and the effective pore volume is >0.17 ml/g, preferably equal or >0.20 ml/g, it is advantageous that the bulk density be as low as possible. In such cases it is advisable to use an activated carbon having a bulk density of equal to or <420 g/l, preferably <390 g/cm³. FIG. 1, which summarises the results of numerous investigations —see Examples—clearly shows the unforeseen extent to which the specific catalyst consumption a (kg catalyst per t of unreacted cyanogen chloride) is dependent on the effective pore volume defined according to the invention when a washed activated carbon having a BET surface area of at least 1000 m²/g and an Fe content of less than 0.15 wt. % (calculated as $Fe_2O_3$) is used. The specific catalyst consumption is low, in particular when both the rate of deactivation (the method of determination may be found in the Examples) and at the same time the bulk density of the catalyst are as low as possible.

EXAMPLES

The investigations to determine the specific catalyst consumption in the reaction zone during the trimerisation of cyanogen chloride to form cyanuric chloride were carried out in a tubular reactor filled with the activated carbon catalyst being examined. The tubular reactor was cooled by means of a heat-transfer medium; the temperature of the coolant was maintained at 280° C. The test reactor was connected parallel to an operating reactor. The gaseous cyanuric chloride formed was condensed after having left the reactor and the liquid product was converted into the solid aggregate state by being sprayed into cooled chambers.

The ratio of the length of the reactor to the cross-section of the reactor was 39. During continuous operation, a temperature profile developed along the longitudinal axis of the reactor. This profile comprises a heating zone, a reaction zone and a cooling zone. The maximum of the reaction zone, the temperature of which rises with increasing flow rate, moves forward in the direction of the flow, with increasing deactivation of the catalyst. The rate of deactivation ($U_{deact}$) was determined by constructing time-dependent temperature profiles from temperature-measuring points arranged along the reactor.

FIG. 2 shows that with increasing operating time, the hot-spot of the reaction zone moves through the complete set of measuring points arranged one behind the other. The actual determination of the rate of deactivation was commenced by a so-called preliminary deactivation of the catalyst—at that time, the "hot-spot" developed near to the inlet to the reactor. The preliminary deactivation of the catalyst lasts for about 12 hours at a flow rate of cyanogen chloride of 1.1 kg per hour. FIG. 2 shows a typical progression of the deactivation. The rate of deactivation in cm/t ClCN can be determined from the distance of the temperature-measuring points and the average quantity of cyanogen chloride (measured from maximum to maximum). The specific catalyst consumption in the reaction zone can be determined from the rate of deactivation ($V_{deact.}$), the reactor geometry (cross-sectional area F) and the bulk density ρ, in accordance with the following equation:

$$a\left[\frac{\text{kg cat.}}{\text{t ClCN}}\right] = u_{Deact} \cdot \left[\frac{\text{cm}}{\text{t ClCN}}\right] \cdot F[\text{cm}^2] \cdot \rho\left[\frac{\text{kg}}{\text{m}^3}\right]$$

TABLE 1

Activated carbon catalysts used

| Catalyst (No.) | Raw material | Wash | Ash content (wt. %) | Fe content (as $Fe_2O_3$) (wt. %) | Bulk density (g/l) | BET ($m^2/g$) | Pore volumes ($cm^3/g$) | | |
|---|---|---|---|---|---|---|---|---|---|
| | | | | | | | $V_{micro}$ | $V_{meso}$ | $V_{eff}$*) |
| C1 | Peat | + | 1.67 | 0.00 | 403 | 1016 | 0.38 | 0.18 | 0.185 |
| C2 | Peat | + | 2.45 | 0.07 | 346 | 1453 | 0.63 | 0.11 | 0.213 |
| C3 | Hard coal | + | 2.24 | 0.03 | 410 | 1217 | 0.51 | 0.17 | 0.212 |
| C4 | Wood | + | 2.18 | 0.28 | 375 | 1523 | 0.64 | 0.09 | 0.205 |
| C5 | Pine wood | − | 8.01 | 0.16 | 406 | 1290 | 0.58 | 0.11 | 0.200 |
| C6 | Coconut | + | 0.42 | 0.00 | 373 | 1459 | 0.59 | 0.04 | 0.157 |
| C7 | Peat | + | 2.46 | 0.07 | 434 | 1213 | 0.50 | 0.08 | 0.165 |
| C8 | Coconut | + | 1.66 | 0.01 | 430 | 1110 | 0.45 | 0.07 | 0.147 |

*) $V_{eff} = 0.25\, V_{micro} + 0.5\, V_{meso}$

Table 2 shows the rate of deactivation u and the specific catalyst consumption a in the reaction zone using the activated carbons given in Table 1, the flow rate of ClCN being 4.4 kg per hour in all the tests.

TABLE 2

Rate of deactivation V and specific catalyst consumption a in the reaction zone

| Catalyst No. | u (cm/t ClCN) | a kg cat./t ClCN |
|---|---|---|
| C1 | 29 | 1.05 |
| C2 | 21 | 0.65 |
| C3 | 25 | 0.92 |
| C4*) | 35 | 1.18 |
| C5*) | 40 | 1.46 |
| C6*) | 35 | 1.18 |
| C7*) | 28 | 1.09 |

Temperature of the heat-transfer medium: 280° C.
*) activated carbon catalyst not according to the invention The tests show that the specific catalyst consumption in the reaction zone depends considerably on the effective pore volume and the bulk density of the catalyst. As a result of a decreased consumption of catalyst, not only is the cost of the catalyst decreased, but at the same time the availability of the plant is increased owing to decreased standstill times and the economic efficiency of the process thereby likewise increased.

What is claimed is:

1. Process for producing cyanuric chloride, comprising trimerisation of cyanogen chloride in the presence of a washed activated carbon having a BET surface area of at least 1000 $m^2/g$ and an Fe content of less than 0.15 wt. %, calculated as $Fe_2O_3$ at a temperature of at least 250° C., wherein an activated carbon having an effective pore volume $V_{eff}$ of equal to or greater than 0.17 ml/g is used, $V_{eff}$ is obtained from pores having a pore diameter in the range of 0.5 to 7 nm.

2. Process according to claim 1, wherein the effective pore volume $V_{eff}$ of the activated carbon is calculated from the sum $V_{eff}=0.25V_{micro}+0.5V_{meso}$, $V_{micro}$ represents pores having a diameter of less than 2 nm and $V_{meso}$ represents pores having a diameter of 2 to 30 nm.

3. Process according to claim 1 wherein $V_{eff}$ of the activated carbon used is at least 0.2 ml/g.

4. Process according to claim 1, wherein the activated carbon has a bulk density of equal to or less than 420 g/l.

5. Process according to claim 1, wherein the activated carbon has a BET surface area of at least 1200 $m^2/g$ and $V_{eff}$ is at least 0.2 ml/g.

* * * * *